United States Patent
Friedrich

(10) Patent No.: US 11,167,113 B2
(45) Date of Patent: *Nov. 9, 2021

(54) TWO-PIECE CATHETER SECUREMENT SYSTEM AND METHOD FOR USING SAME

(71) Applicant: Novum Vascular, LLC, San Antonio, TX (US)

(72) Inventor: Terrell Friedrich, Helotes, TX (US)

(73) Assignee: NOVUM VASCULAR, LLC, San Antonio, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/992,078

(22) Filed: May 29, 2018

(65) Prior Publication Data

US 2018/0272109 A1 Sep. 27, 2018

Related U.S. Application Data

(63) Continuation of application No. 14/482,932, filed on Sep. 10, 2014, now Pat. No. 9,981,111.

(60) Provisional application No. 61/875,915, filed on Sep. 10, 2013.

(51) Int. Cl.
*A61M 25/02* (2006.01)

(52) U.S. Cl.
CPC ....... *A61M 25/02* (2013.01); *A61M 2025/024* (2013.01); *A61M 2025/028* (2013.01); *A61M 2025/0246* (2013.01); *A61M 2025/0266* (2013.01)

(58) Field of Classification Search
CPC ............ A61M 25/02; A61M 2025/024; A61M 2025/0266; A61M 2025/0246
See application file for complete search history.

(56) References Cited

U.S. PATENT DOCUMENTS

| | | |
|---|---|---|
| 4,397,647 A | 8/1983 | Gordon |
| 6,361,523 B1 | 3/2002 | Bierman |
| 6,572,588 B1 | 6/2003 | Bierman et al. |
| 6,582,403 B1 | 6/2003 | Bierman et al. |
| 6,770,055 B2 | 8/2004 | Bierman et al. |
| 7,922,697 B2 | 4/2011 | Beran |
| 8,016,792 B2 | 9/2011 | Wright et al. |
| 8,137,326 B2 | 3/2012 | Chesnin |
| 8,197,447 B2 | 6/2012 | Wright |
| 2007/0249980 A1 | 10/2007 | Carrez et al. |
| 2007/0293800 A1 | 12/2007 | McMaken et al. |
| 2010/0016801 A1 | 1/2010 | Rosenberg et al. |
| 2012/0109070 A1 | 5/2012 | Elsamahy et al. |
| 2012/0136314 A1 | 5/2012 | Ciccone et al. |
| 2013/0072875 A1 | 3/2013 | Rosenberg et al. |
| 2016/0317786 A1 | 11/2016 | Friedrich |

*Primary Examiner* — Bradley J Osinski

(74) *Attorney, Agent, or Firm* — Kilpatrick Townsend & Stockton LLP

(57) ABSTRACT

A two-piece catheter securement system has a fixation pad with an adhesive undersurface and an antimicrobial flap. On an upper surface of the pad are cooperative first attachment members. An upper capture and retention shell has an outer shell wall. The first and second ends of the shell may have a plurality of slots for capturing and retaining administration and catheter tubing. The shell has an inner shell ceiling having a plurality of spaced apart second attachment members thereon. The first and second attachment members are aligned to cooperatively engage when the shell is urged into releasable engagement with the pad with the slots capturing and retaining the tubes.

5 Claims, 10 Drawing Sheets

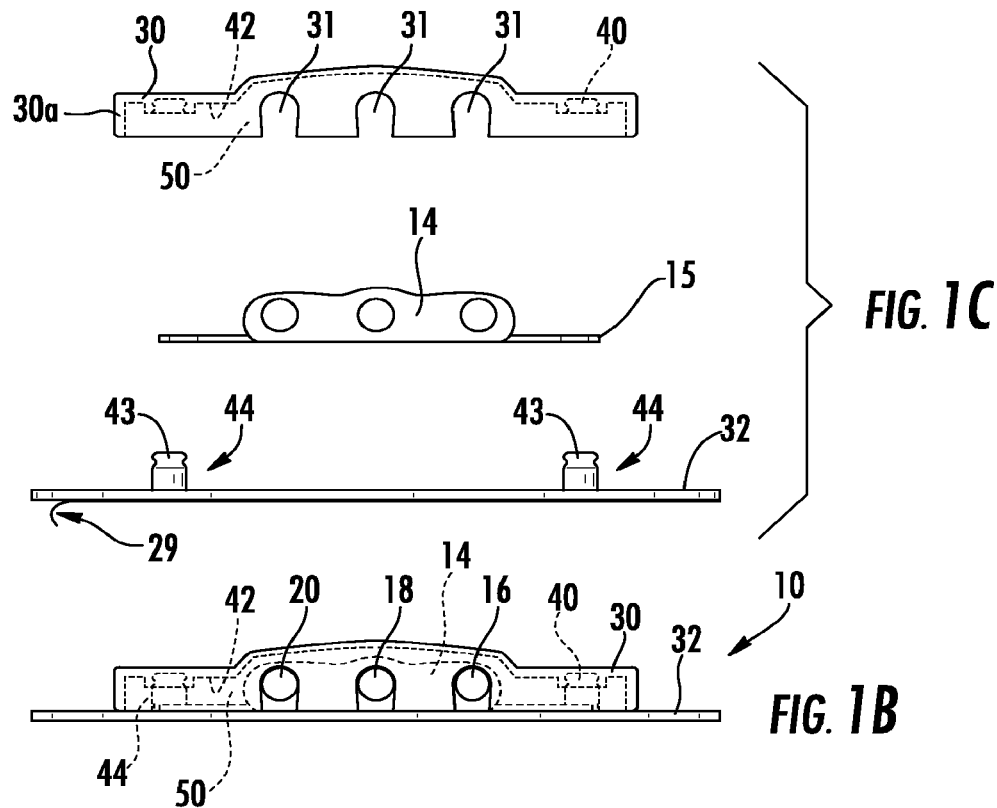
FIG. 1C
FIG. 1B
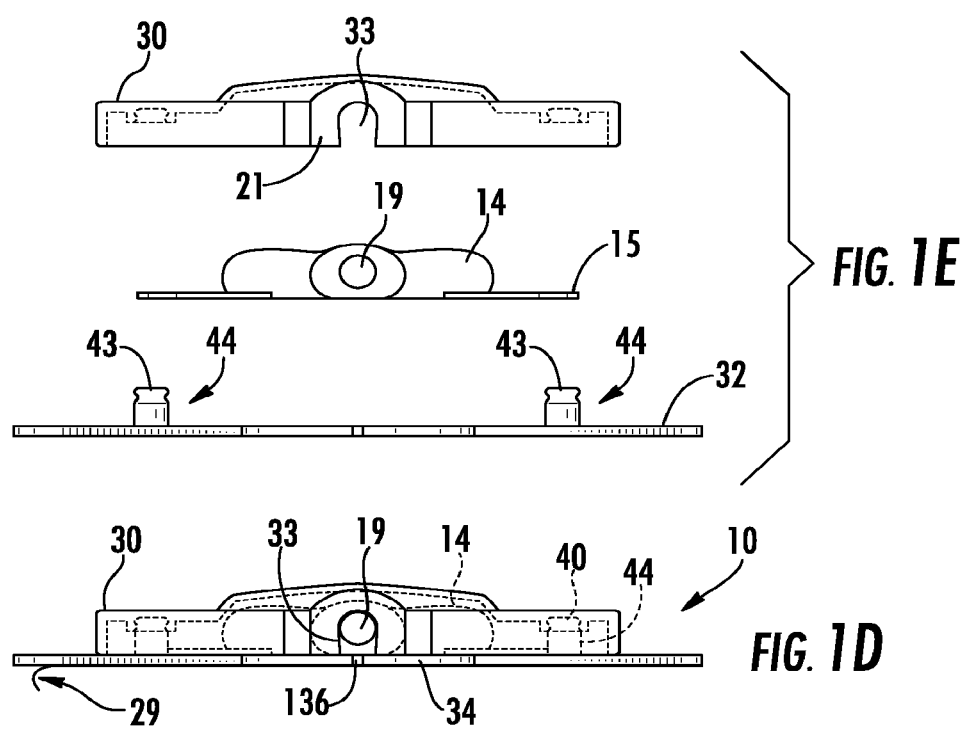
FIG. 1E
FIG. 1D

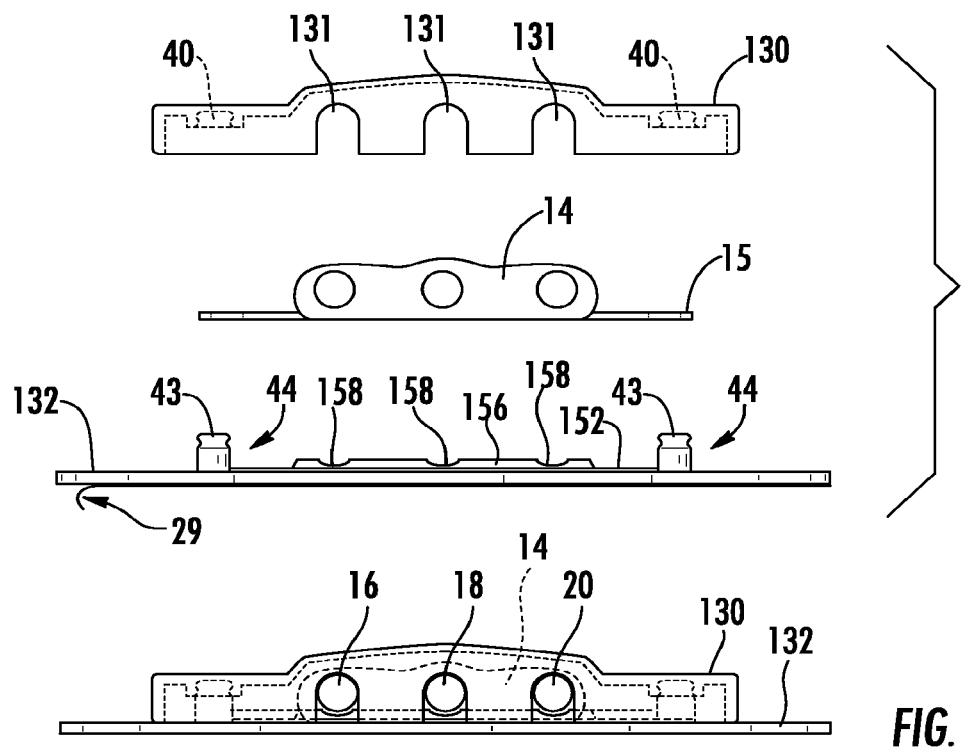
FIG. 3A
FIG. 4A
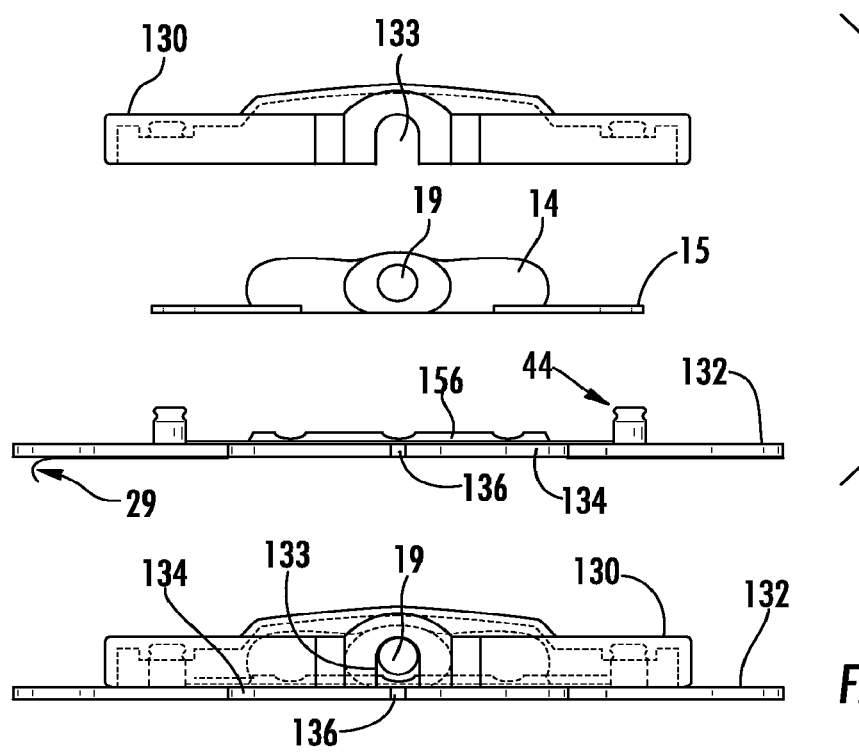
FIG. 3B
FIG. 4B

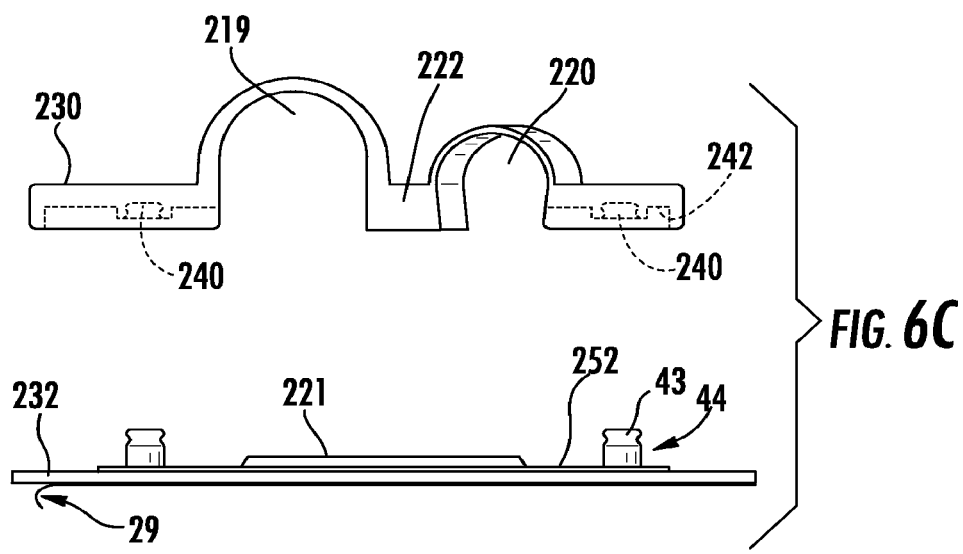
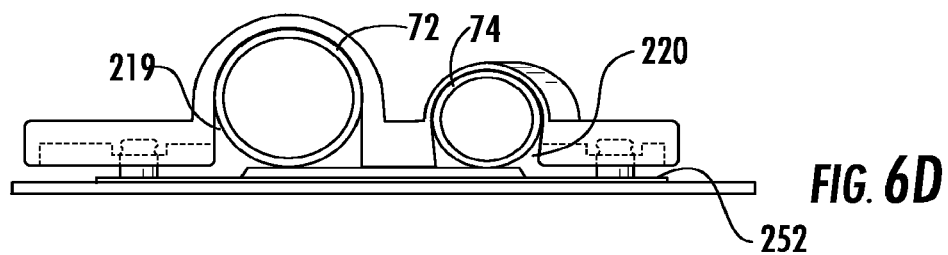
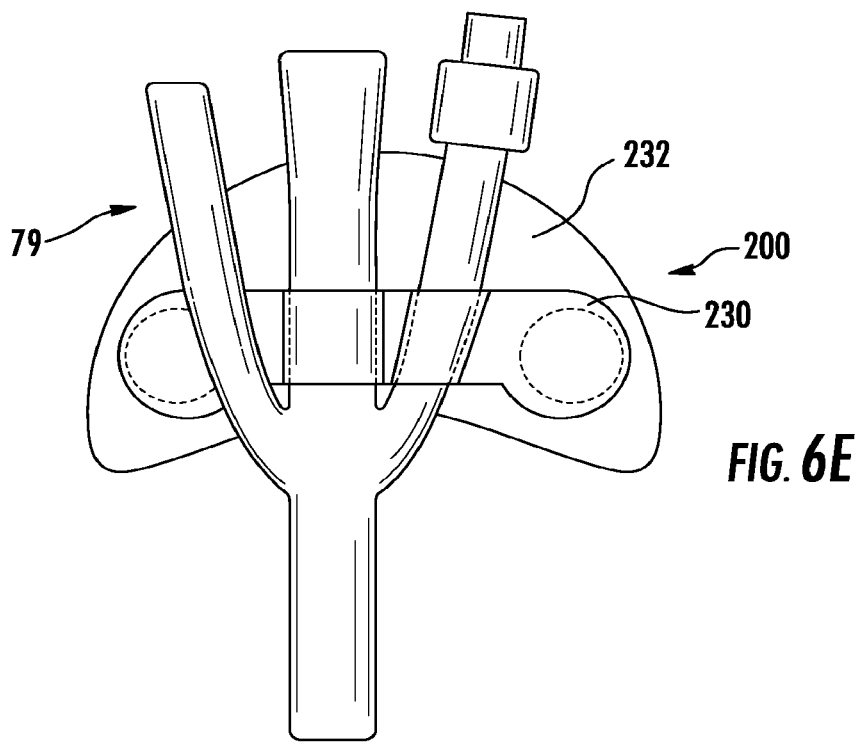

TWO-PIECE CATHETER SECUREMENT SYSTEM AND METHOD FOR USING SAME

CROSS-REFERENCE TO RELATED APPLICATION

This application is a Continuation Application of and claims priority to Non-Provisional patent application Ser. No. 14/482,932 filed Sep. 10, 2014, which claims priority to U.S. Provisional Patent Application Ser. No. 61/875,915 filed Sep. 10, 2013. The disclosures of the above-identified patent applications are hereby incorporated by reference in their entirety.

BACKGROUND OF THE INVENTION

The present invention relates to a catheter securement system for the prevention of the accidental removal or malpositioning a variety of catheter styles. More specifically, the present invention relates to a two-piece catheter securement device having a shell-like capture and retention cover releasably engagable with a lower fixation pad adhesively attachable to the body of a patient.

It is known in the art relating to catheters that after insertion of a catheter through a patient's skin into a vein, the catheter must be secured to prevent the catheter from slipping out of the patient's vein. Commonly, surgical tape is used to hold the catheter hub or tubing connected to the catheter to the patient's skin. Oftentimes, this method is ineffective to permanently, securely anchor the catheter and to prevent catheter movement.

Further, inadvertent movement of a catheter while the catheter is inserted in a vein is a leading cause of premature catheter failure. When a catheter moves in a vein, it scrapes and pokes the inner wall of the vein, thereby irritating the vein. Repeated movement of the catheter thereby causes sufficient irritation of the vein to require the catheter to be removed and a new catheter inserted in a different location along the same vein or in an entirely new vein. This is costly as it results in a waste of resources. Also, repeated movement of an inserted catheter can cause migration of the catheter in the vein or worse, may lead to the catheter being removed from the vein. Therefore, a need exists for effective anchoring/securement devices for catheters.

Moreover, it is also known to use a catheter dressing with pressure sensitive adhesives to fully secure and protect a catheter such as a Peripherally Inserted Central Catheter ("PICC"). PICCs are typically made of polyurethane or silicone based materials. Due to the low surface energy of silicones, adhesives from dressings do not fully anchor or grip to silicone substrates as well as polyurethane materials. Thus, PICC movement will occur when a PICC covered with a dressing is tugged or pulled.

While there are numerous prior art securement devices, as described below, most recent prior art devices utilize a complex mechanical arrangement of parts which secure a catheter by engaging and securing the catheter hub and hub wings. The prior art devices generally are integral units which include a cover attached or hinged to a base, but not separable.

The present invention offers a unique solution to the problem of immobilizing the catheter assembly. It may be applied to various catheters or conduits exiting or entering the patient's body including, but not limited to, central line catheters, peripheral intravenous (IV) catheters, urinary drainage catheters including the Foley catheter, gastric feeding tubes, chest tubes, Huber needles utilizing subcutaneous ports, and other catheters or tubing that require immobilization.

Certain terminology is used in this disclosure for convenience only and is not to be taken as a limitation on the present invention. The terms "distal" and "proximal" refer, respectively, to directions closer to and away from the insertion tip of a catheter in an implantable catheter assembly. The terminology includes the words specifically mentioned, derivatives thereof and words of similar import.

U.S. Pat. No. 8,137,326 discloses a hub for a triple lumen catheter assembly of the type commonly used in the field of medical devices and, more particularly, to catheters and catheter assemblies. Such hubs accommodate a multiplicity of extension tubes, commonly referred to as administration tubes, at a proximal side of the hub and at least one catheter tube on a distal side of the hub extending to a distal tip inserted into the patient's body.

The prior art hub has a body portion with a distal end and a proximal end and a central region from which laterally, outwardly extend a pair of suture wings with suture openings therethrough to facilitate anchoring the hub to the patient after the catheter implantation procedure is complete. In many medical procedures the hub is not sutured to the patient even though the hub has wings and suture openings. Nothing in U.S. Pat. No. 8,137,326 teaches or discloses a catheter securement device.

A catheter securement device to secure silicone winged peripherally inserted central catheters (PICCs) is disclosed in U.S. Pat. Pub. No. US2012/0109070A1. This securement device is designed to be used to anchor catheters having wings. The device includes a fabric, sheet-like, anchoring member having a top surface, an opposite bottom surface, a base portion, and a pair of strap portions extending from the base portion. The anchoring member includes an adhesive on the bottom surface in the base portion and is generally adhesive free on the top surface in the base portion.

The anchoring member also includes an adhesive on the top surface in the strap portions and is generally adhesive free on the bottom surface in the strap portions. The base portion is mountable on a patient's skin intermediate a catheter hub having wings, and each strap portion is foldable over the base portion and one catheter hub wing to secure the catheter hub.

Further, features of the strap portions include leg and foot members, perforation lines, fold lines which require precise folding and placement to secure the catheter hub. The hub is basically wrapped and secured by the fabric sheet and stuck to the patient; the device, while seemingly simple in parts, is very complex to utilize.

U.S. Pat. No. 8,197,447 teaches a venipuncture site protector which includes a securement and a cover mounted to the securement. The cover includes a proximal end having a front wall with a tube receiving slot. The cover also includes a distal end having an arch that forms an opening that lies on a vertical plane that is substantially perpendicular to the securement. The cover is permanently mounted on the securement once the cover is attached to the securement.

Another prior art universal catheter securement device is disclosed in U.S. Pat. No. 8,016,792, as having a complex arrangement of a cover or shell member attachable to a base which when engaged restrains longitudinal movement of catheter hub wings between front and rear locating elements. With smaller or narrower catheters, a gap is left between the wings and the locating elements which would normally allow the catheter to shift longitudinally under force (e.g. with pulling on the catheter tubes). However when the cover is closed, the catheter body and/or wings are clamped tightly by the capture elements. Thus, in the device of U.S. Pat. No. 8,016,792, an inner cover or shell surface engages with the catheter hub and/or wings.

U.S. Pat. No. 7,922,697 discloses yet another catheter securement device having an adhesive backed base pad with a fixed plate and a rotatable adjustable plate permanently affixed to the base pad. Posts are on the fixed plate and the adjustable plate to secure a winged catheter. There is no cover or shell cooperatively engaging the base to secure tubing to and from a catheter hub.

U.S. Pat. Nos. 6,770,055 and 6,582,403 both relate to universal catheter anchoring systems having a cover section hingedly attached to a base member of a retainer permanently affixed to an anchor pad with adhesive disposed on a lower or under side of the anchor pad. The system includes at least one post movably attached to either the base or the cover and arranged so as to lie at least partially between the cover and the base when the cover is in a closed position.

SUMMARY OF THE INVENTION

The present invention provides a two-piece securement system for a catheter assembly. The first piece is a lower fixation pad with a plurality of first attachment members which may be upwardly depending attachment studs similar to the male section of a snap fastener. The second piece is a upper capture and retention shell having a plurality of second attachment members which may be stud receiving sockets similar to the female section of a snap fastener. The second attachment members are disposed on an inner surface or ceiling of the shell and are aligned to cooperatively releasably engage and secure the studs of the first piece when the shell (second piece) is urged into engagement with the lower fixation pad (the first piece). The inner portion of the shell is maintained in a space apart relationship from the hub and hub wings of the catheter assembly wherein only the administrative tubing and the catheter tubing are captured and retained in slotted openings in the proximal and distal ends of the shell.

The present invention differs from the prior art in that the shell is not permanently attached to the lower fixation pad. The securement shell may be reused. The shell makes no positive engagement or connection with the catheter hub body or hub wings other than prevent lateral or longitudinal movement of the catheter. Immobilization is achieved by restricting the movements of the hub proximate the connection of the administrative tubing and the catheter tubing extending to or from the hub body. No direct connection is made with the hub or hub wings and no friction or pressure is applied to the catheter hub or wings. The hub is free to move transversely (up and down) within the securement device but not laterally or longitudinally.

BRIEF DESCRIPTION OF THE DRAWINGS

The above mentioned features and steps of the invention and the manner of attaining them will become apparent, and the invention itself will be best understood by reference to the following description of the embodiments of the invention in conjunction with the accompanying drawings wherein:

FIG. 1 illustrates the securement device cooperating with a three lumen peripherally inserted central catheter (PICC).

FIG. 1B shows a proximal end view of the assembled device with a catheter hub therein.

FIG. 1C illustrates an exploded proximal end elevation view showing the capture and retention shell with the catheter hub disposed intermediate the fixation pad.

FIG. 1D shows a distal end view of the assembled device with a catheter hub therein.

FIG. 1E illustrates an exploded distal end elevation view showing the capture and retention shell with the distal portion of the catheter hub disposed intermediate the fixation pad.

FIG. 2A1 is a proximal end elevation view of the pad of FIG. 2A.

FIG. 2A11 is a distal end elevation view of the pad of FIG. 2A.

FIG. 3A shows an exploded proximal end view of the embodiment of FIGS. 2 and 2A showing the capture and retention shell with the catheter hub disposed intermediate the fixation pad.

FIG. 3B shows an exploded distal end view of the embodiment of FIGS. 2 and 2A showing the distal end of the shell with the distal end of the hub intermediate the distal end of the fixation pad.

FIG. 4A illustrates a proximal end elevation view of the assembled securement device with the hub therein.

FIG. 4B illustrates a distal end elevation view of the assembled securement device with the hub therein.

FIG. 6C is an exploded proximal end view of the Foley variant securement device.

FIG. 6D is a proximal end elevation view of the assembled Foley variant.

FIG. 6E illustrates how a three lumen Foley would be attached the Foley embodiment of the securement device.

DETAILED DESCRIPTION OF THE PREFERRED EMBODIMENT

Figure 1:
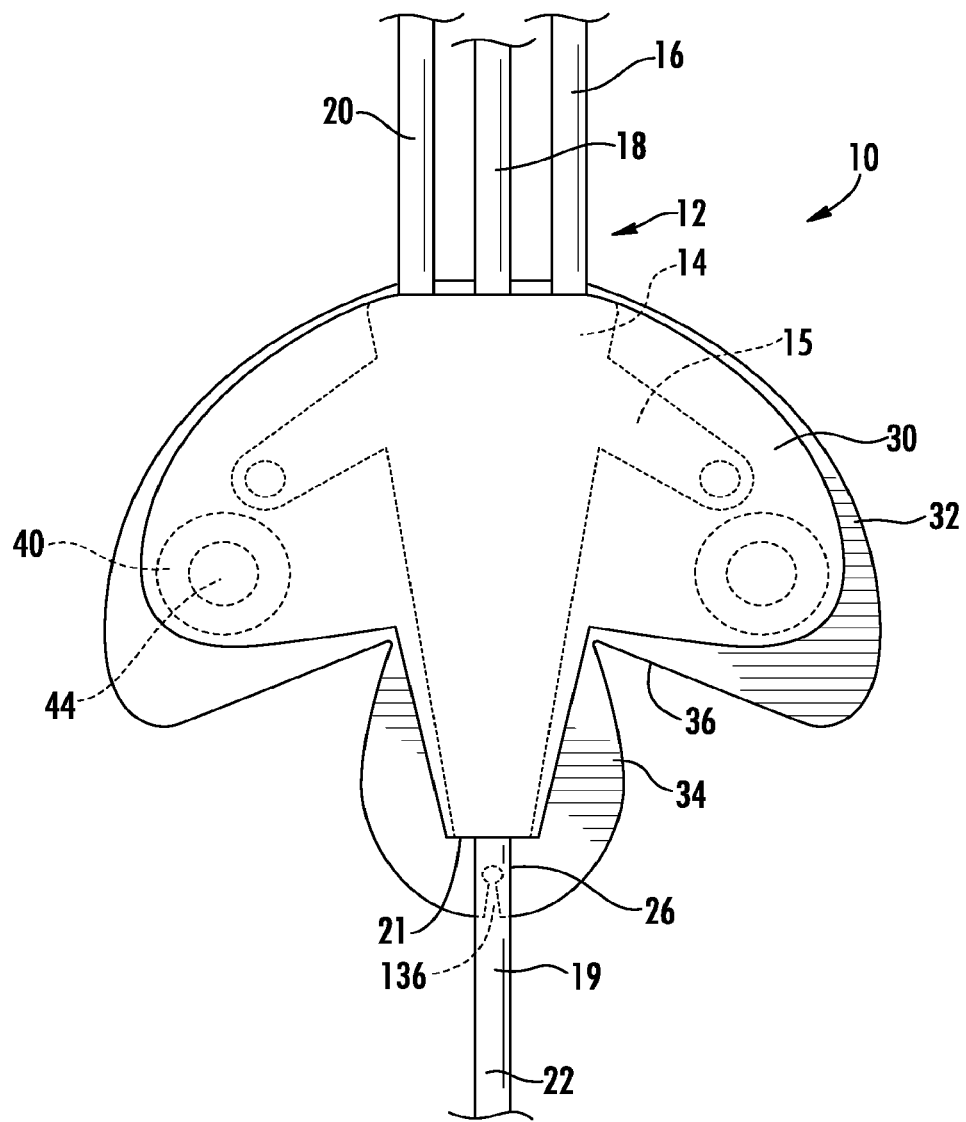
FIG. 1 illustrates a top plan view of the securement device of the present invention with the catheter hub secured beneath the upper capture and retention shell and the fixation pad.

In the drawings, like numerals indicate like elements throughout. The embodiments illustrated below are not intended to be exhaustive or to limit the invention to the precise form disclosed. These embodiments are chosen and described to best explain the principle of the invention and its application and practical use and to enable others skilled in the art to best utilize the invention.

A two-piece catheter securement system 10 is seen in FIG. 1 for securing a triple lumen catheter 12, a hub 14 with wings 15, three extension/administration tubes 16, 18, 20, and a catheter tube or conduit into a patient's body 19. Catheter tube 19 has distal end portion 22 extending to a distal tip (not shown), and also a proximal end portion 26 that extends to and is connected to the hub 14.

FIG. 1 illustrates a top plan view of the securement system 10 of the present invention with the catheter hub 14 disposed beneath and within an upper capture and retention shell or cover 30 and a fixation pad 32. FIG. 1 illustrates the securement system cooperating with a three lumen peripherally inserted central catheter (PICC). An anti-microbial flap 34 extends distally from a distal end 36 of the pad 32 as will be described below.

FIG. 1B shows a proximal end view of the assembled present inventive system with a catheter hub 14 therein. As may be seen in FIG. 1B, neither the hub 14 nor the hub wing 15 of the catheter body contact the inner surface of the capture and retention shell 30. No pressure is applied to the hub or wings.

An exploded proximal end elevation view of the securement system 10 and a catheter hub 14 are illustrated in FIG. 1C. The shell 30 is shown above the hub 14 with the fixation pad 32 below the shell and hub. It will be understood by one of skill in the art that the pad 32 is to be supported on and stuck to the patient when in use. A non-adhesive, removable backing sheet 29 is removed from the underside of the pad 32 to expose the adhesive surface.

FIG. 1C shows that the shell or cover 30 is provided on its proximal-most end with a plurality of tapering slots 31 designed to capture and retain administration tubes 16, 18, 20 when the shell is placed over the hub 14 and hub wings 15 (see FIG. 1E). The shell 30 is also provided on its distal-most end with at least one tapering slot 33 designed to capture and retain catheter tube 19 when the shell is placed over the hub 14 and hub wings 15. A plurality of attachment members 40 are disposed in a spaced apart relationship on the inner ceiling surface 42 of the shell. The members 40 may be socket-like receptacles, similar to those of a snap fastener assembly, which are aligned to accept, receive, and retain cooperating attachment members 44 which are affixed in space apart relationship on fixation pad 32.

Tubes 16, 18, 19, 20 are shown in FIG. 1B as each having a circular cross-section, although, optimally, their cross-sections may have some other shape, such as oval, generally triangular, or semi-cylindrical. The outside diameter of the tube is slightly larger than the width of the tapered slots 31 and 33 and, therefore, when the tubes are inserted into the slots, there is a slight compression of the tubes and the tubes are retained in the slots.

The shell 30 has a generally open space 50 inwardly of the shell walls 30a to provide an area to receive the hub and wings as may be seen in FIG. 1B. There is a gap or space between the hub 14 and the inner shell surface 42.

Attachment members 44 are shown in FIGS. 1C and 1E as being upwardly depending studs or posts (male sections) which have heads 43 which snap in place in the socket receptacles (the female sections) of members 40. Alternatively, the female sections may be affixed to the pad 32 while the male sections may be affixed to the shell ceiling. Further, the heads 43 may be replaced with a groove around the top portion of the stud which snaps into the female socket as is well known in the snap fastener art.

A snap fastener (also called press stud, popper or tich) is a pair of interlocking discs, made out of metal or plastic. The circular lip under one disc fits into a groove on the top of the other, holding them fast until a certain amount of force is applied.

An assembled distal end view of the invention of FIG. 1 is shown in FIG. 1D. It may be seen that the catheter tube 19 is retained and secured in tapered slot 33 in the shell distal end wall 21.

An exploded distal end elevation view of the securement system 10 and a catheter hub 14 are illustrated in FIG. 1E. The shell 30 is shown above the hub 14 with the fixation pad 32 below the shell and hub.

Turning again to FIG. 1, flap 34 extending from the distal end 36 of the pad 32 is a section of flexible material which may include the foam padding of the fixation pad, fabric, paper, or the like which may be impregnated with or have on an outer surface of the flap 34 an antimicrobial composition. The flap 34 has a slit or cut 34a to allow the flexible flags to be wrapped close to the insertion site and, thereby, disperse antimicrobial compounds at the site to reduce the likelihood of infection.

Figure 2:
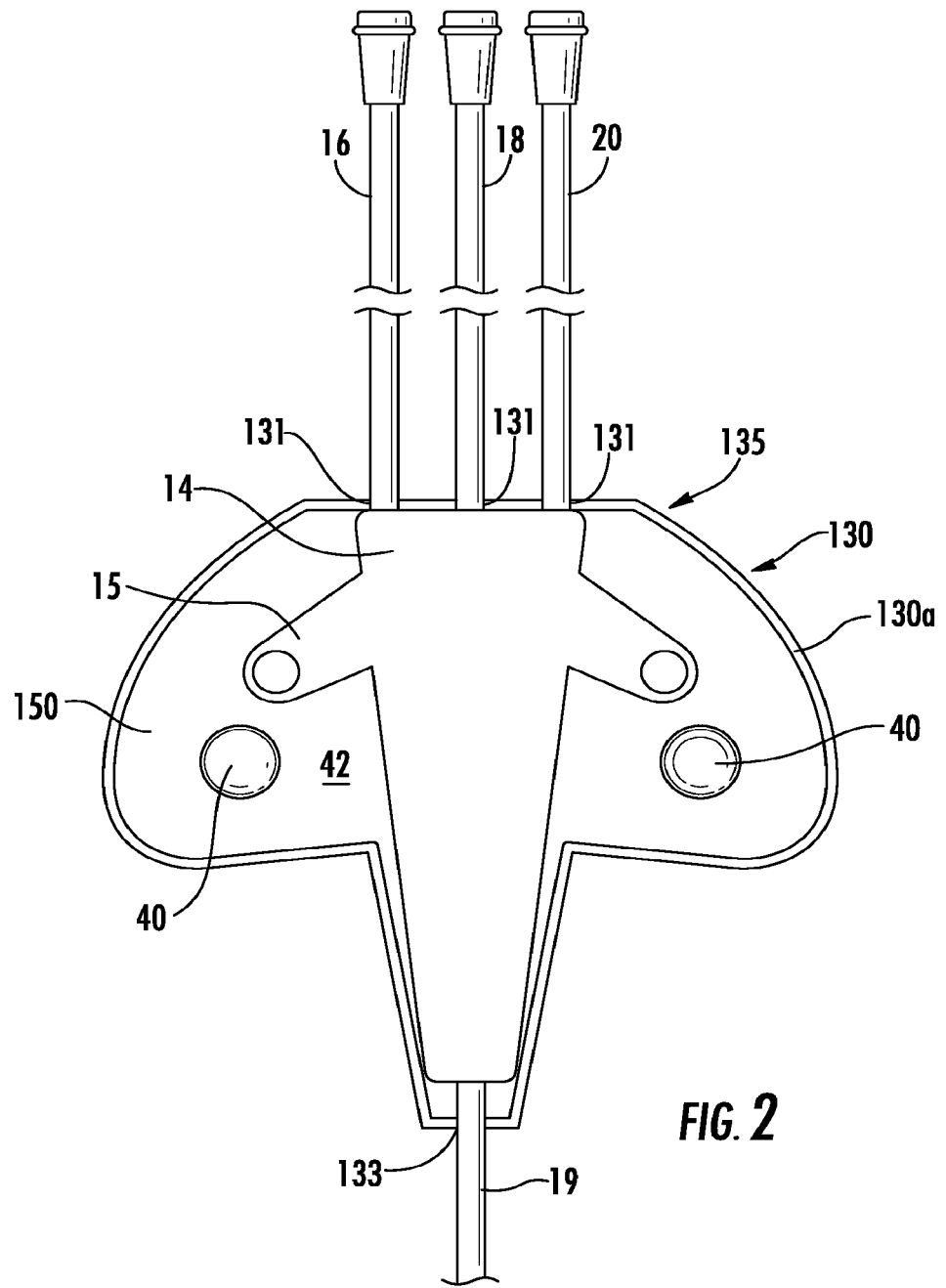
FIG. 2 illustrates an underside plan view of the capture and retention shell of another embodiment of the securement device of the present invention with the catheter hub disposed within open space within the shell and the administration lumens at the proximal end secured in retention notches in the proximal end wall of the shell.

FIG. 2 illustrates an underside plan view of a capture and retention shell 130 of another embodiment of the present invention with a catheter hub 14 with hub wings 15 disposed within the open area 150 of shell 130. Administration tubes 16, 18, 20 extend from the proximal end of the hub 14 while catheter tube 19 extends from the distal end of the hub 14.

As with and described in the embodiment of FIG. 1, the FIG. 2 embodiment has a plurality of attachment members 40 disposed in a spaced apart relationship on the inner ceiling surface 42 of the shell 130.

The shell 130 has an outer shell wall 130a. The proximal-most end of the shell 130 has a plurality of notches 131 (see also FIG. 2B) designed to accommodate administration tubes 16, 18, 20 when the hub 14 and hub wings 15 are disposed within the open area 150. At the distal-most end of the shell 130 a notch 133 is designed to accommodate catheter tube 19. (Tom—please check this last sentence.)

Figure 2A:
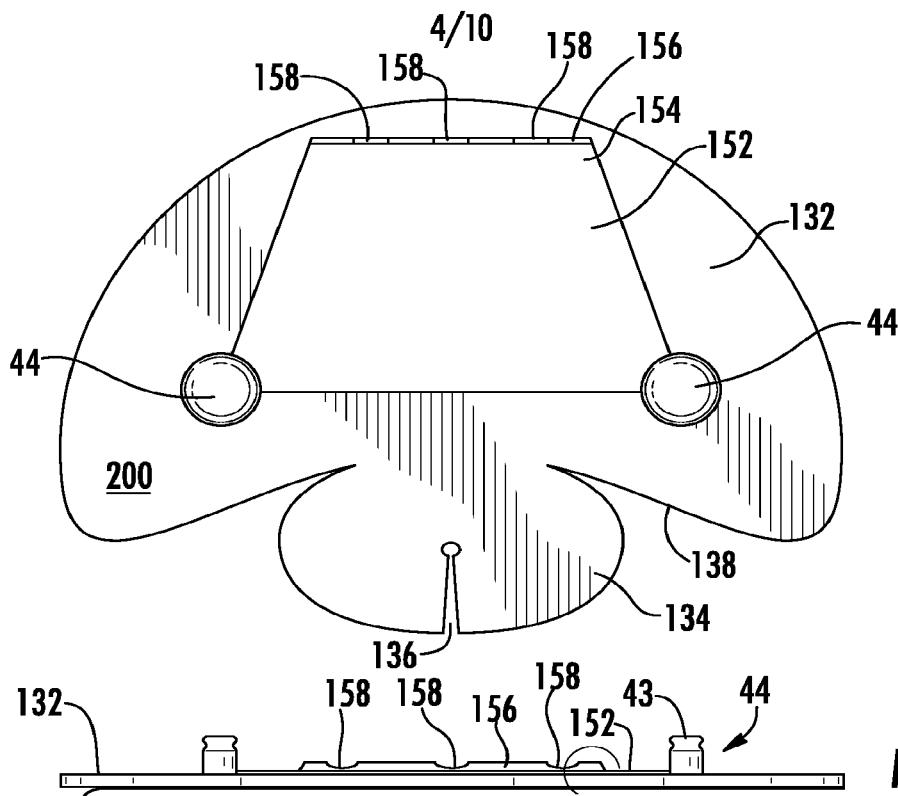
FIG. 2A is a top plan view of the upper side of the fixation pad showing the rigid plate or stiffener disposed on the upper surface of the pad with retention notches or slots in a proximal end wall on the upper surface of the pad. An anti-microbial flap extends from a distal end of the pad with a catheter tube positioning slot.

The fixation pad 132 which cooperates with shell 130 is illustrated in FIG. 2A. FIG. 2A is a top plan view of the upper side of the fixation pad 132 showing a rigid plate or stiffener member 152 affixed to the pad 132. The proximal-most end 154 of the plate 152 has a raised wall 156 with a plurality of notches 158 sized to accommodate the outside diameter of the administration tubes 16, 18, 20. A flap 134 extends from the distal end 136 of the pad 132. The flap 134 is of a flexible construction much like a thin fabric sheet.

Attachment members 44 are attached and disposed in a spaced apart relationship on the upper surface 200 of the pad 132. Preferably, members 44 are connected to or engaged with the stiffener member 152 to facilitate connection with and disengagement from attachment members 40 on the shell 130. The stiffener 152 eliminates flexing of the pad 132 when the fasteners 40 and 44 are snapped or unsnapped.

As described above, antimicrobial flap 134 is attached to the distal end 136 of the pad 132. The flap 134 may have an antimicrobial preparation or composition on the underside of the flap. The flap has a cut or slit 136 in its distal-most end of the flap. This allows the medical personnel to place the flap close to the insertion site to reduce the likelihood of contamination at the insertion site without interfering with the catheter.

Figure 2B:
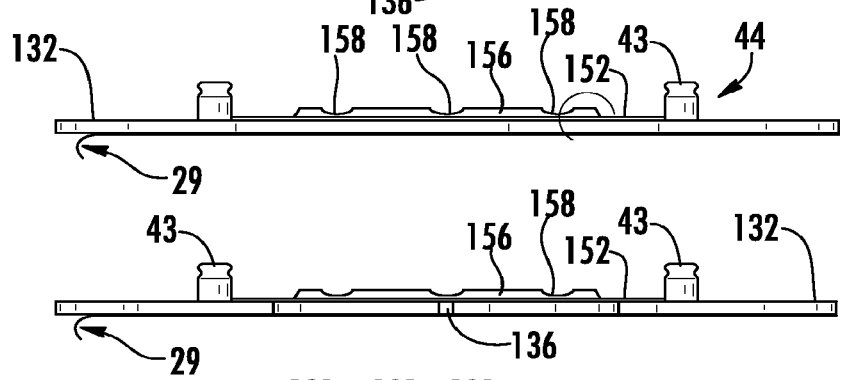
FIG. 2B illustrates an underside view of the capture and retention shell of another embodiment of the present invention showing attachment members disposed in a spaced apart relationship on the inner ceiling surface of the shell. A provisional front end wall is shown with retention slots or notches and a distal end alignment channel is provided in the distal end of the shell.
Figure 2B:
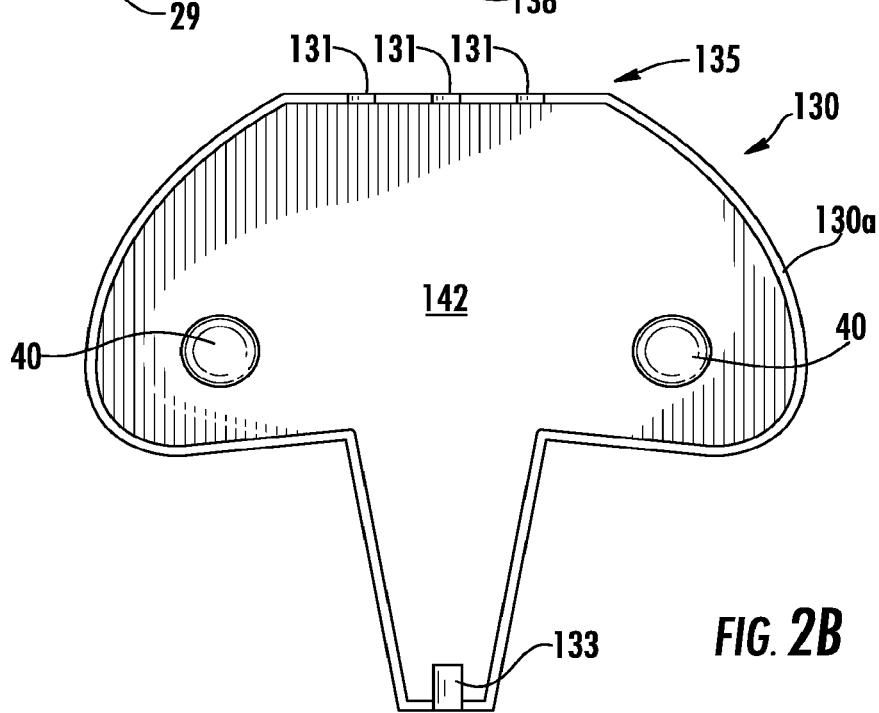

FIG. 2A1 is a proximal end elevation view of the pad of FIG. 2A and FIG. 2A" is a distal end elevation view of the pad of FIG. 2A. FIG. 2B illustrates an underside view of the capture and retention shell 130 of FIG. 2. The shell 132 has an outer shell wall 130a and an inner ceiling 142. The proximal-most end of the shell 135 has a plurality of notches 131 sized to accommodate administration tubes 16, 18, 20 while the distal-most end has a notch 133 sized to accommodate catheter tube 19.

Attachment members 40 are attached to and disposed in a spaced apart relationship on ceiling 142. Attachment members 40 are disposed so as to cooperatively align with members 44 on the pad 132 when the members 40 and 44 are urged into releasable engagement. FIG. 3A illustrates an explode proximal end view of the securement system of FIGS. 2 and 2A showing the shell 130 with catheter hub 14 with wings 15 disposed intermediate of the fixation pad 132.

FIG. 3B illustrates an exploded distal end view of the securement system of FIGS. 2 and 2A showing the shell 130 above hub 14 (with wings 15) and aligned for releasable engagement with fixation pad 132.

In the securement system of FIGS. 2 and 2A, the notches 131 cooperate with the notches 158 in wall 156 to align the tubing 16, 18, 20. The notches may be sized to have a diameter slightly smaller than the outside diameter of the tubing or about the same size.

FIGS. 4A and 4B show proximal and distal end views, respectively, of the assembled system shown in FIGS. 3A and 3B, respectively. It should be noted in FIGS. 4A and 4B that the tubing 16, 18, 19, 20 is slightly small in diameter than the cooperating notches 131 and 133.

Figure 5:
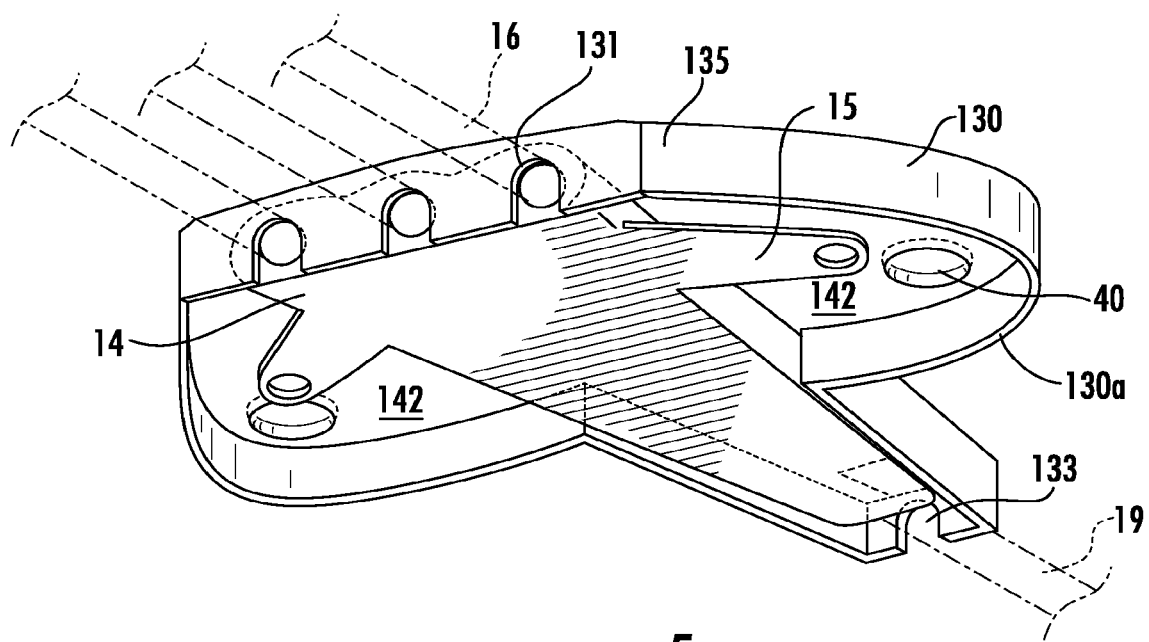
FIG. 5 is a perspective view of the device of FIGS. 2, 2A, and 2B.

A perspective view of the system of FIGS. 2 and 2B is illustrated in FIG. 5. The fixation pad 132 is not shown for clarity purposes.

Figure 6:
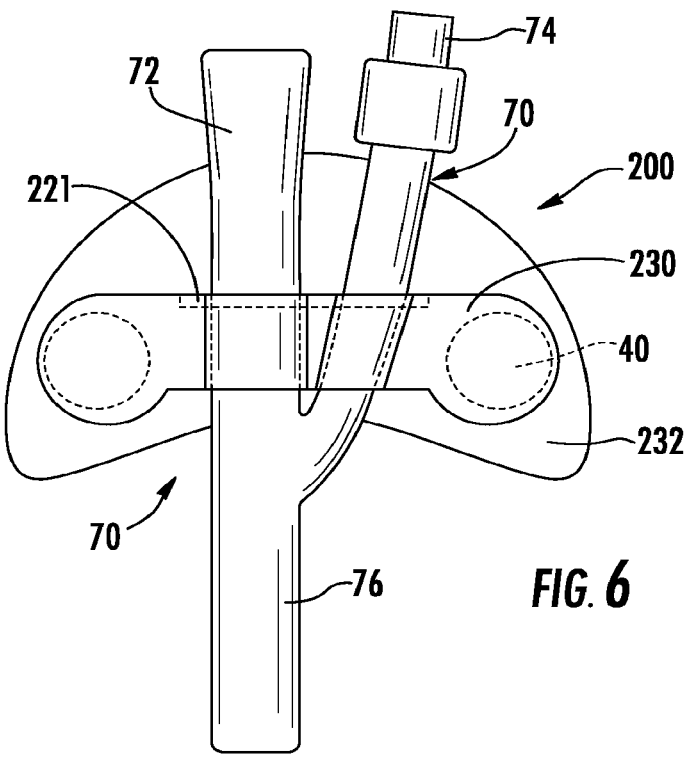
FIG. 6 illustrates a top plan view of another embodiment of the present invention used in connection with a Foley catheter variant having two administration lumens.

FIG. 6 illustrates a securement system 200 of the present invention for use with a Foley catheter. A Foley catheter is a flexible tube that is often passed through the urethra into the bladder. It is the most common type of indwelling urinary catheter. A Foley catheter may also be used to ripen the cervix during induction of labor. Such catheters may have triple, double, or single lumen arrangements.

In FIG. 6 a double lumen Foley catheter 70 is secured by securement system 200 having a shell member 230 and a fixation pad 232. The shell 230 is releasably engaged with pad 232 by attachment members 40 and 44.

System 200 is designed to not allow rotation of the catheter 70 such as is allowed with prior art securement devices with a swiveling, non-fixed single point of attachment of the capture mechanism to the adhesive base. Such rotation, or swivel, of the prior art catheter may result in the introduction of bacteria into the urinary tract causing infection. The use of a plurality of fixed attachment points of the capture mechanism (shell) to the fixation pad as shown in Fig. reduces or eliminates rotational motion, or "pistoning" of the catheter in the urethra during leg movement.

Figure 6A:
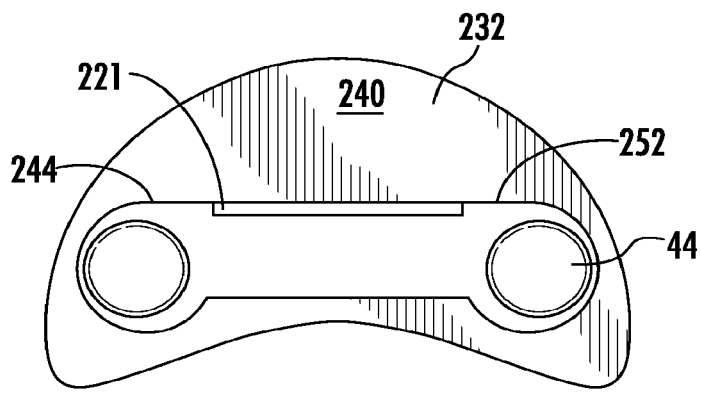
FIG. 6A is a top plan view of the fixation pad for the Foley variant.

As may be seen in FIG. 6, Foley catheter 70 has a drainage leg 72 and a balloon leg 74 and a main catheter tube 76. These legs and the catheter tube are held in fixed positions by the shell 230 which is releasably connected to the fixation pad 232 by the attachment member 40 and 44. In FIG. 6A, the upper surface 240 of the pad is provided with a stiffener plate 252 which extends laterally across a mid-portion of the pad. Along the proximal edge 244 of the stiffener 252 extends a raised, friction ridge or rib 221. At opposite, lateral ends of the stiffener are attachment members 44 which are complimentary portions of a snap fastener assembly (either male or female sections) as described above. The underside of the pad 232 is provided with an adhesive which affixes the pad to the patient as would be understood by one skilled in the art.

Figure 6B:
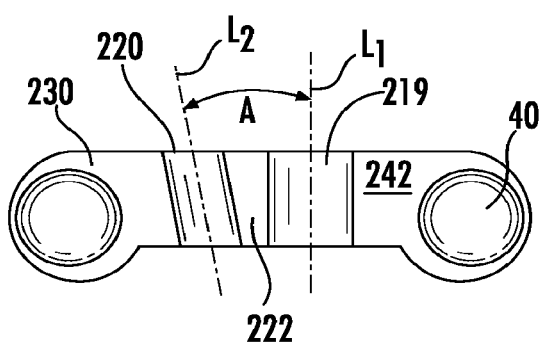
FIG. 6B is an underside view of the shell for the Foley variant.

Cooperating with pad 232 is the capture and retention shell 230 as shown in FIG. 6B. FIG. 6B is an underside view of the shell 230 showing channels 219 and 220 which are sized to accept, receive, and retain legs 72 and 74 respectively. Channel divider wall 222 separates channels 219 and 220.

The longitudinal axes L1 and L2 of channels 219 and 220 are disposed at an angle A to one another to accommodate the standard Foley catheter. The angle A further ensures that the catheter 70 will not rotate.

Attachment members 40 are attached to and disposed on the inner ceiling 242 of the shell 230 and are complimentary to attachment members 44 on the pad. The attachment members 40 and 44 align and are releasably engagable when the shell 230 is snapped to the pad 232. FIG. 6C is an exploded proximal end view of securement system 200 showing the shell 230 with channels 219 and 220 with divider wall 222 between them. Attachment members 240 are shown attached to the inner ceiling 242 of the shell. Below the shell in FIG. 6C is the fixation pad 232 with friction rib 221 on the proximal edge of the stiffener 252 and attachment member 44.

An illustration of an assembled securement system 200 retaining and fixing Foley catheter 70 is shown in FIG. 6D. As may be seen the legs 72 and 74 are retained in channels 219 and 220 respectively with the lower portions of the legs engaged with friction rib 221 when the complimentary attachment members 40 and 44 are urged into releasable engagement. Thus, should a pulling or twisting force be applied to either tube 72 or 74 so as to attempt to withdraw catheter tube 76, the catheter tube will not rotate or piston as may occur with prior art devices. The frictional forces created by the tubes 72 and 74 being urged against the rib 221 reduces the likelihood of the catheter 70 rotating or moving.

FIG. 6E illustrates how a three legged Foley catheter 79 would be attached to the securement system 200.

Figure 7:
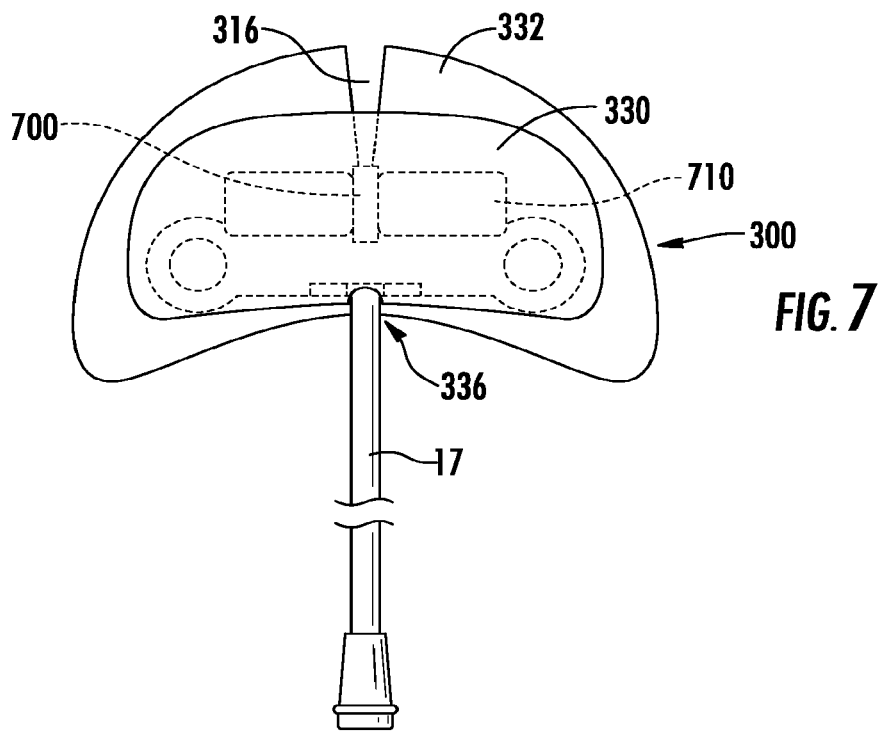
FIG. 7 is a top plan view of an embodiment of the present invention for use with a Huber needle catheter assembly.
Figure 7A:
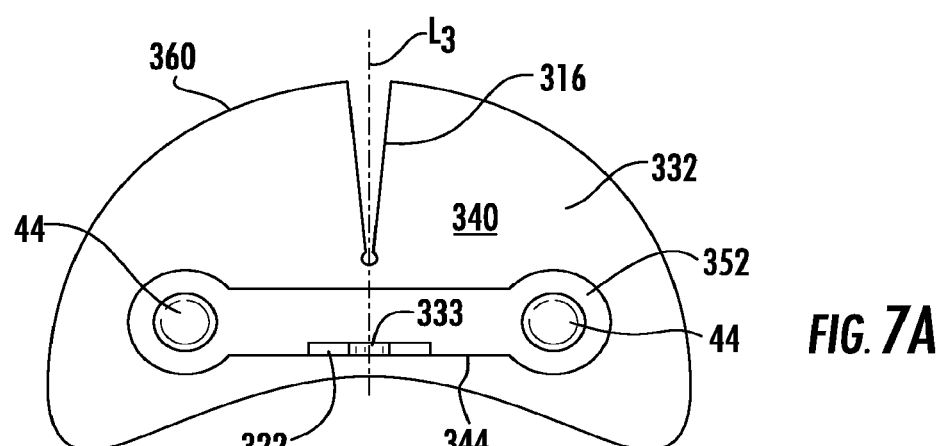
FIG. 7A illustrates the fixation pad for use in the Huber variant.
Figure 7B:
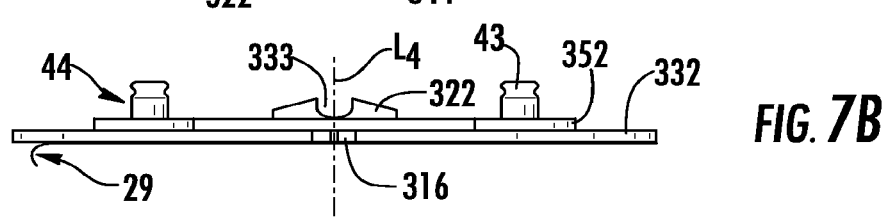
FIG. 7B shows a proximal end elevation view of the fixation pad with the distal fenestration slot and the proximal end tube locater ridge.
Figure 7C:
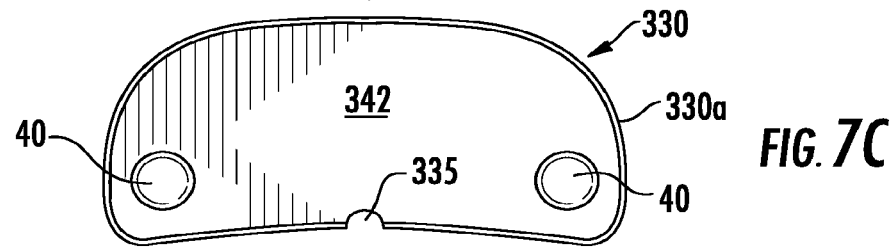
FIG. 7C is an underside view of the shell with the attachment member on the inner ceiling of the shell.
Figure 7D:
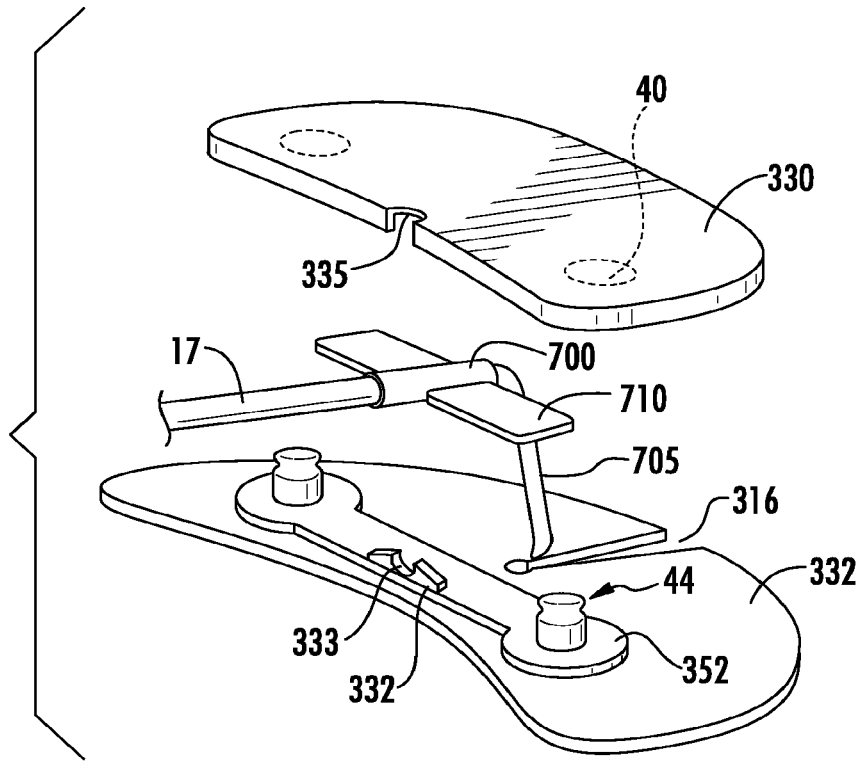
FIG. 7D is an exploded perspective view of the embodiment of FIGS. 7-7C.
Figure 7E:
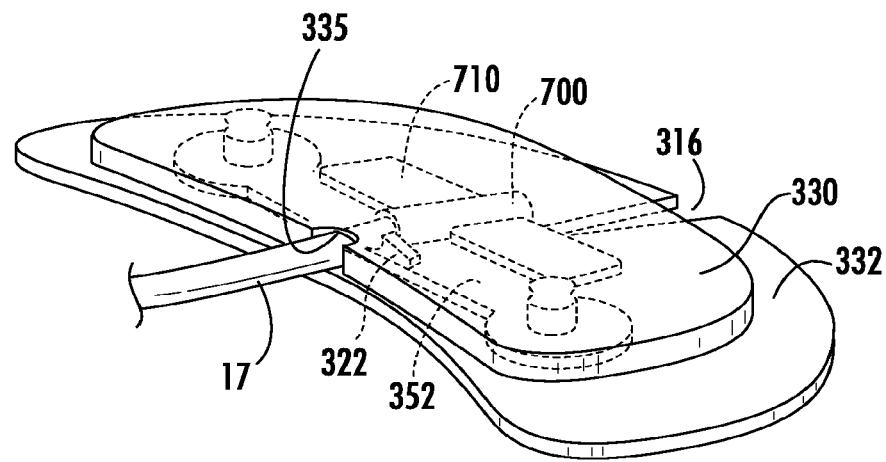
FIG. 7E is a perspective view of the assembled Huber variant of the present invention.

FIGS. 7-7E relate to another embodiment of the present inventive securement system for use with a Huber needle. Huber needles are an alternative to other infusion delivery systems. They are used in conjunction with patient implanted ports and are used for patient therapies requiring repeated vascular access and long-term fluid therapies. They are conduits into the patient's body.

The Huber needle embodiment of the present invention allows the placement and stabilization of the Huber needle in the subcutaneous port. The stabilization of the Huber needle is achieved without any pressure on the wings or the body portion of the Huber needle itself. This is an important aspect of the present invention because it allows the Huber needle to rise in clearance as the patient possibly loses body fat and the skin thickness above the port decreases.

FIG. 7 shows a top plan view of the securement system 300 which is useful with a Huber needle. A shell or cover 330 is shown attached to a fixation pad 332 securing there between a Huber needle body 700 having wings 710. Extension tube 17 extends from the distal end 336 of the shell/pad combination. Drugs and therapies are delivered via tube 17.

FIG. 7A illustrates a top plan view of the fixation pad 332 used with the Huber needle embodiment. A fenestration slot 316 is provided in the pad to locate the downwardly depending needle 705 (FIG. 7D) which extends into the subcutaneous port (not shown). Extending laterally across the mid-portion of the upper surface 340 is a stiffener plate 352. Along a mid portion of the distal edge 344 of the stiffener 352 extends a conduit locator channel 322 with a notch 333. As may be further seen in FIG. 7A, the notch in locator 322 is in longitudinal alignment with the longitudinal axis L3 of the fenestration slot 316.

At opposite lateral ends of the stiffener plate 352 are attachment members 44 which are complimentary portions of a snap fastener assembly (either male or female sections) as previously described with other embodiments. As with other fixation pads described herein, the underside of pad 332 is provided with a protected 29 adhesive surface which affixes the pad to the patient.

FIG. 7B illustrates an elevation view of pad 332 from the front end 360 of the pad. The locator channel 322 is shown on the stiffener plate 352 between the spaced apart attachment members 44. The fenestration slot 316 is shown in vertical alignment L4 with the notch 333 in locator 322.

An underside view of shell 330 is shown in FIG. 7C. The shell has an outer wall 330 a with an opening 335 and an inner ceiling 342. Attachment members 40 are disposed on ceiling 342 and are in alignment with members 44 on the pad 332 such that the members 40 and 44 are releasably engaged when the shell 330 is urged into engagement with the pad 332. Shell opening 335 aligns with the notch 333 when the system 300 is assembled.

FIG. 7D illustrates an exploded perspective view of the embodiment 300 of FIGS. 7-7C with a Huber needle assembly having an insertion needle or conduit into a patient's body 705, body 700 and wings 710 shown intermediate the shell 330 and the pad 332.

In operation the needle 705 is inserted into the subcutaneous port (not shown). The clinician slides the fixation pad 332 under the body or hub 700 and wings 710 via the fenestration slot 316. A non-adhesive protective strip 29 is removed to expose the adhesive under-surface of the pad. (The adhesive material may be impregnated with an antimicrobial preparation.)

The Huber needle is held in place when the shell 330 is urged into releasable engagement with the pad 332 and attachment members 40 and 44 snap together. This places pressure on the extension tubing 17 as it passes through opening 335 and rests in the notch 333 in locator 322. The needle 705 is secure in the fenestration slot 316.

FIG. 7E shows a top perspective view of the assembled securement system 300.

Although the invention has been described with reference to specific embodiments, this description is not meant to be construed in a limited sense. Various modifications of the disclosed embodiments, as well as alternative embodiments of the inventions will become apparent to persons skilled in the art upon reference to the description of the invention. It is, therefore, contemplated that the appended claims with cover such modifications that fall within the scope of the invention.

What is claimed is:

1. A two-piece catheter securement system for use with two or more administration tubes each having an outside diameter and at least one catheter tube and a catheter hub, the system comprising:
   a lower fixation pad consisting of an upper surface and a lower surface, the lower surface having an adhesive covered by a removable backing sheet, the upper surface having a plurality of notches sized to accommodate the outside diameter of the two or more administration tubes and a plurality first attachment members that are spaced apart; and
   an upper capture and retention shell sized to fit over the catheter hub and having first and second end walls, the second end wall having one or more tapering openings for capturing and retaining the one or more administration tubes, the first end wall having at least one tapering opening for capturing and retaining the at least one catheter tube, the upper capture and retention shell being detachable from the lower fixation pad and having a plurality of second attachment members aligned to engage the plurality of first attachment members when the shell engages with the lower fixation pad, the one or more tapering openings capturing and retaining the tubes, and the inner shell surface at the second attachment members allowing vertical movement of the hub between the upper surface of the lower fixation pad and the inner shell surface of the upper capture and retention shell.

2. The two-piece catheter securement system of claim 1 wherein the first attachment members are vertical studs and the second attachment members are sockets, the sockets adapted to releasably engage and secure the studs therein in an interference fit when the shell engages with the lower fixation pad.

3. The two-piece securement system of claim 2 wherein the lower fixation pad has a first locator rib on a first end of the upper surface, the first locator rib having at least one receiving slot adapted to locate and receive the at least one catheter tube, and a second locator rib on a second end of the upper surface, the second locator rib having one or more receiving slots adapted to locate and receive the one or more administrative tubes.

4. The two-piece catheter securement system of claim 2 further comprising a flexible flap extending from a first outer edge of the fixation pad.

5. The two-piece catheter securement system of claim 4 wherein the flexible flap has an antimicrobial compound on or in an outer surface of the flexible flap.

* * * * *